(12) United States Patent
Hunter, Jr.

(10) Patent No.: US 6,592,509 B1
(45) Date of Patent: Jul. 15, 2003

(54) ELECTROMAGNETIC STIMULATOR

(76) Inventor: Thomas W. Hunter, Jr., 2220 New Hope Rd., Hendersonville, TN (US) 37075

( * ) Notice: Subject to any disclaimer, the term of this patent is extended or adjusted under 35 U.S.C. 154(b) by 0 days.

(21) Appl. No.: 10/067,051

(22) Filed: Feb. 4, 2002

(51) Int. Cl.[7] ................................................ A61N 2/00
(52) U.S. Cl. ........................................................ 600/9
(58) Field of Search ............................. 600/13, 15, 14, 600/26; 607/3, 51, 64, 72, 46, 76, 52; 602/2; 320/108, 138

(56) References Cited

U.S. PATENT DOCUMENTS

| | | | | |
|---|---|---|---|---|
| 3,648,708 A | * | 3/1972 | Haeri | 607/64 |
| 3,893,462 A | | 7/1975 | Manning | |
| 3,915,151 A | * | 10/1975 | Kraus | 600/13 |
| 4,282,475 A | * | 8/1981 | Milton | 320/138 |
| 4,556,051 A | * | 12/1985 | Maurer | 600/14 |
| 4,757,804 A | * | 7/1988 | Griffith et al. | 600/13 |
| 4,915,151 A | | 4/1990 | Sato et al. | |
| 5,267,939 A | * | 12/1993 | Liboff et al. | 600/13 |
| 5,318,561 A | * | 6/1994 | McLeod et al. | 600/14 |
| 5,518,495 A | * | 5/1996 | Kolt | 600/13 |
| 5,518,496 A | * | 5/1996 | McLeod et al. | 600/14 |
| 5,527,259 A | * | 6/1996 | Grace et al. | 600/14 |
| 5,669,868 A | * | 9/1997 | Markoll | 600/14 |
| 5,743,844 A | * | 4/1998 | Tepper et al. | 600/14 |
| 5,951,459 A | * | 9/1999 | Blackwell | 600/13 |
| 6,007,476 A | | 12/1999 | Wascher et al. | |
| 6,024,691 A | * | 2/2000 | Tepper et al. | 600/13 |
| 6,042,531 A | | 3/2000 | Holcomb | |
| 6,208,115 B1 | * | 3/2001 | Binder | 320/108 |
| 6,235,251 B1 | | 5/2001 | Davidson | |
| 6,280,376 B1 | | 8/2001 | Holcomb | |

* cited by examiner

*Primary Examiner*—Eric F. Winakur
*Assistant Examiner*—Nikita Veniaminov
(74) *Attorney, Agent, or Firm*—Michael E. McKee

(57) ABSTRACT

An electromagnetic stimulator system and a method for treating body tissue utilizes includes an electrically-conductive band having an interior opening, a body of electrically-conductive material secured to the band in electrically-conducting relationship therewith, and an insulated coil encircling the body of the electrically-conductive material so that when a DC current is conducted through the coil, an electromagnetic field is induced through the body of electrically-conductive material which, in turn, induces an electromagnetic field within the interior opening of the band. A battery charger is used to delivering DC current through the coil from an AC electrical outlet so that by positioning the body tissue to be treated within the electrically-conductive band and delivering DC current through the coil, the body tissue positioned within the band is exposed to the electromagnetic field induced within the interior opening of the band.

15 Claims, 3 Drawing Sheets

ELECTROMAGNETIC STIMULATOR

BACKGROUND OF THE INVENTION

This invention relates to electromagnetic stimulator systems and relates more particularly, to such systems for use in the medical field to promote healing and/or to reduce pain.

Apparatus are known which utilize electricity for generating an electrical or magnetic field which, in turn, can be used for medical purposes. One such apparatus, shown and described in U.S. Pat. No. 3,915,151, employs a pair of sheet-like electrodes which, during use, are disposed on opposite sides of a region of a body to be treated with the apparatus.

It is an object of the present invention to provide a new and improved electromagnetic stimulator system for use in the medical field to promote healing or to reduce pain.

Another object of the present invention is to provide such a stimulator system which is uncomplicated in construction yet effective in operation.

SUMMARY OF THE INVENTION

This invention resides in an electromagnetic stimulator system for treating body tissue and a method for treating body tissue.

The system of the invention includes an electrically-conductive band having an interior opening sized to accept body tissue desired to be treated with the stimulator system, a body of electrically-conductive material secured to the band in electrically-conducting relationship therewith, and an insulated coil encircling the body of the electrically-conductive material so that when a DC current is conducted through the coil, an electromagnetic field is induced through the body of electrically-conductive material which, in turn, induces an electromagnetic field within the interior opening of the band. The system also includes means for delivering DC current through the coil so that by positioning the body tissue to be treated within the electrically-conductive band and delivering DC current through the coil, the body tissue positioned within the band is exposed to the electromagnetic field induced within the interior opening of the band.

The method of the invention includes the steps of using the system of the invention. In particular, the system of the invention is provided, the body tissue to be treated is positioned within the electrically-conductive band, and then DC current is delivered through the coil so that the body tissue positioned within the band is exposed to the electromagnetic field induced within the interior opening of the band.

DETAILED DESCRIPTION OF THE ILLUSTRATED EMBODIMENTS

Figure 1:
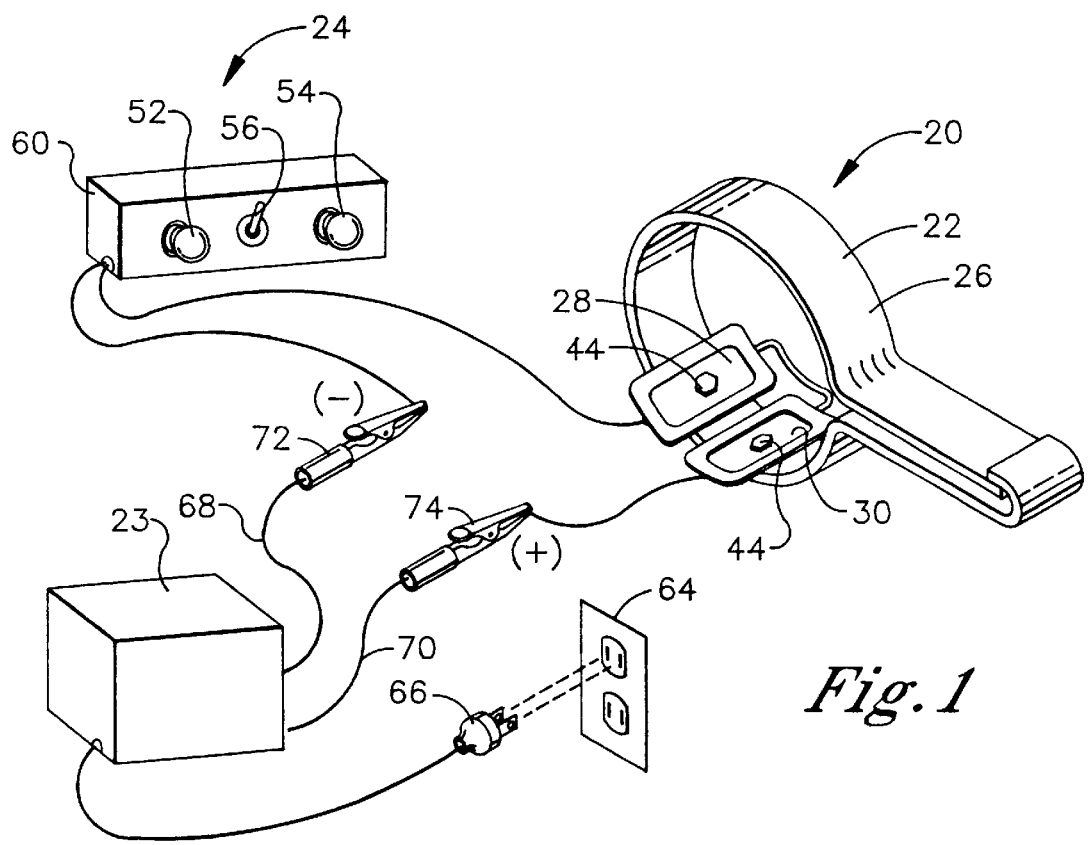
FIG. 1 is a perspective view of an embodiment of the electromagnetic stimulator system within which features of the invention are incorporated.
Figure 2:
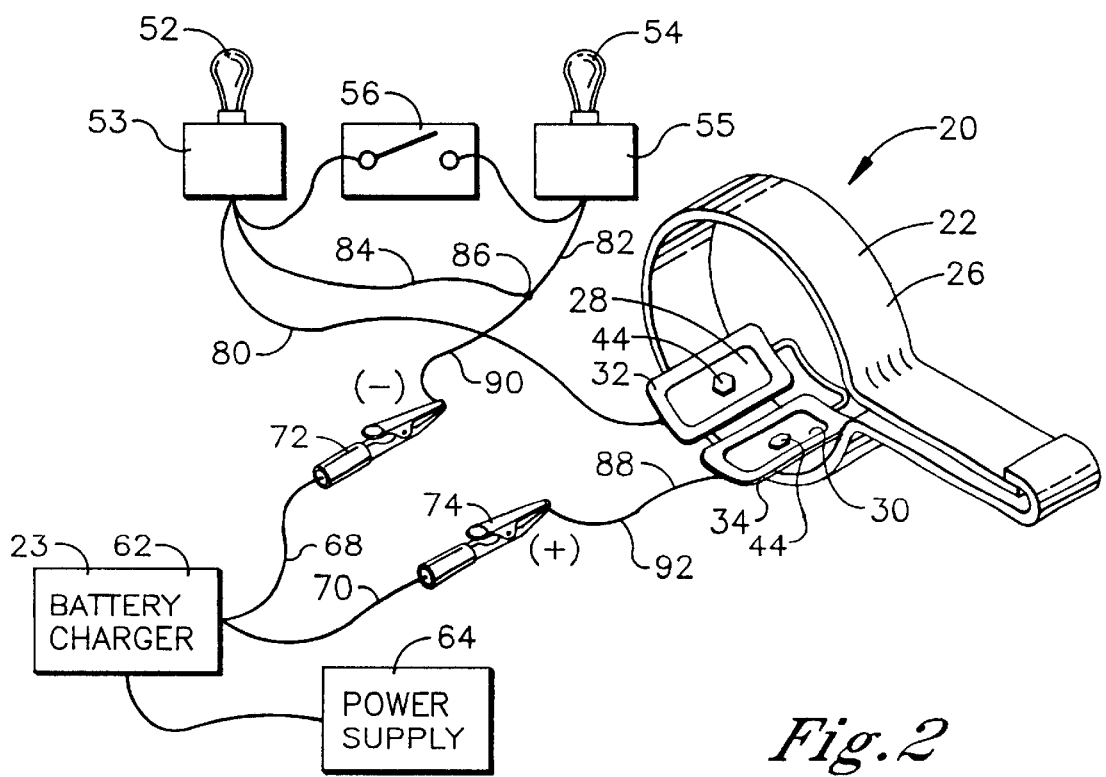
FIG. 2 is a perspective view, similar to FIG. 1, which schematically illustrates the wiring of the FIG. 1 system.

Turning now to the drawings in greater detail and considering first FIGS. 1 and 2, there is illustrated an embodiment of an electromagnetic stimulator system, generally indicated 20, which can be used to treat body tissue in a manner which has been found to promote healing of or to reduce pain within the tissue. The system 20 includes a stimulator device 22 which is positionable about the region of the body tissue to be treated and DC source 23 through which DC current is delivered to the stimulator device 22. In addition, the system 20 includes means, generally indicated 24, for altering the current flow delivered to the device 22 from the DC source 23.

Figure 3:
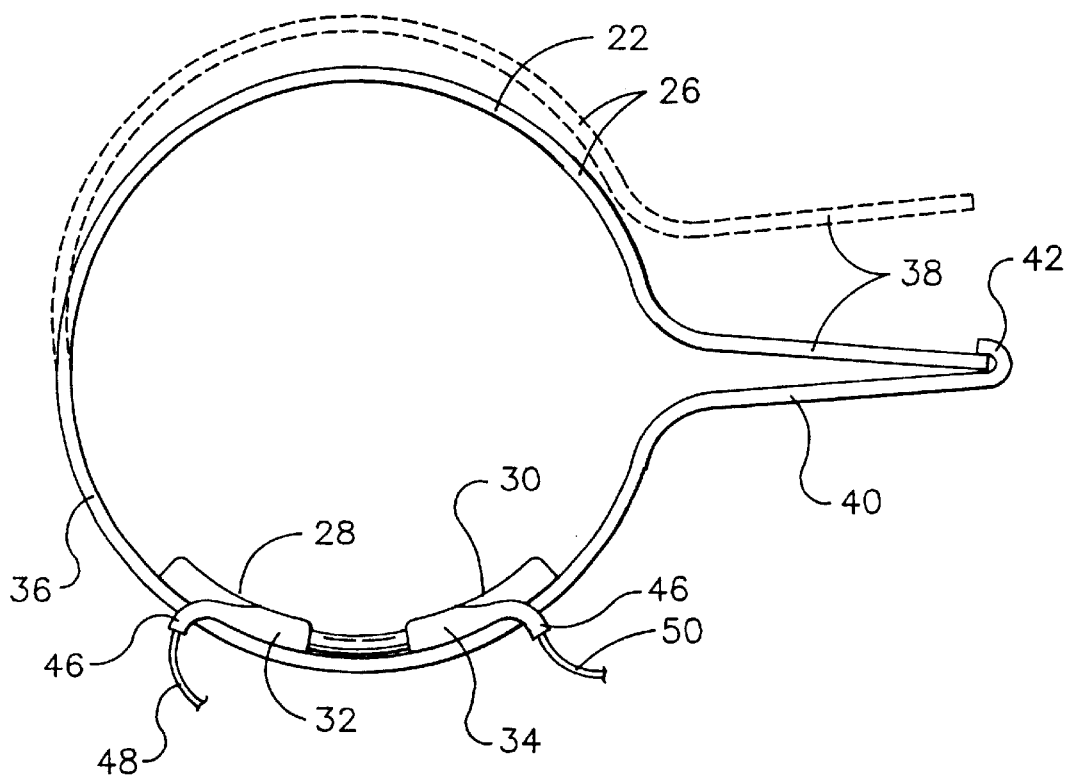
FIG. 3 is a perspective view of the stimulator device of the FIG. 1 system.

With reference to FIGS. 1–3, the stimulator device 22 includes an electrically-conductive band 26 which is sized to be positioned about the region of the body tissue to be treated with the system 20, a pair of electrically-conductive bodies 28, 30 attached to the band 26, and a pair of electrically-conductive coils 32, 34 wherein each coil 32 or 34 encircles a corresponding body 28 or 30. During use of the system 20, DC current is delivered through the coils 32, 34 which, in turn, generates what is believed to be an electromagnetic field within the bodies 28, 30. With the bodies 28, 30 secured to the band 26, a corresponding electromagnetic field is established, or induced, within the interior opening of the band 26 so that by positioning a region of body tissue within the interior opening of the band 26, the body tissue region is exposed to the field established within the band 26.

As best shown in FIG. 3, the band 26 has a relatively small thickness and includes an arcuate section 36 and a pair of linear sections 38, 40 joined to the ends of the arcuate section 36. One of the linear sections 40 terminates in a crook 42 for accepting an end of the other linear section 38 when positioned therein for securing the (terminal) ends of the linear sections 38, 40 together. To detach the linear sections 38, 40 from one another, one linear section 38 is forcibly urged (e.g. in a sideways direction) relative to the other linear section 40 to remove the terminal end of the linear section 38 from within the crook 42 formed in the terminal end of the other linear section 40. With the linear sections 38, 40 detached from one another, the linear sections 38, 40 can be spread apart to, for example, the position illustrated in phantom in FIG. 3 to enlarge the internal diameter of the arcuate portion 36 and thereby facilitate the positioning of the arcuate portion 36 about the region of body tissue to be treated with the system 20. To re-attach the linear sections 38, 40 together for use of the stimulator 22, the linear sections 38, 40 are simply moved toward one another and appropriately manipulated to position the terminal end of the linear section 38 within the crook 42 of the linear section 40. The band 26 of the depicted stimulator device 22 is constructed of steel, but alternative electrically-conductive materials can be employed.

As far as the width of the band 26 is concerned, it is preferable that the width of the band 26 be large enough to span the region of body tissue to be treated with the device 22. The depicted band 26 has a width of about 1.5 inches and an internal diameter of about 8.0 inches and has been found to be sufficient for treating bones of the hand, wrist and ankle areas. However, for treating larger regions of the body, such as a lengthy section of the spine, the width of the portion of the band 26 positionable adjacent the spinal section to be treated would preferably be large enough to span the spinal section to be treated. As an alternative to making the width of the band large enough to span the region to be treated, an electrically-conductive (e.g. steel) plate can be sized to span the region of the body to be treated and fastened to the band 26 so that the effective area of the band positionable adjacent the region to be treated is thereby increased.

With reference again to FIGS. 1–3, each of the electrically-conductive bodies 28, 30 and electrically-conductive coils 32, 34 encircling the bodies 28, 30 of the depicted simulator 22 were taken from the starter of an internal combustion engine and are therefore appropriately sized to cooperatively interfit with one another. In particular, each of the electrically-conductive bodies 28, 30 is provided by a pole shoe of the starter, and each of the electrically-conductive coils 32, 34 is provided by a coil which encircles a corresponding pole shoe of the starter and is held in place thereby. Hence, each coil (i.e. the coil 32 or 34 of the stimulator 22)—which is intended to generate what is believed to be an electromagnetic field in a corresponding pole shoe within a starter—is appropriately sized to closely encircle the pole shoe for generating an electromagnetic field therein when the field coil/pole shoe arrangements are secured within the band 26 and is held in place against the band 26 by the body 28 or 30.

In the depicted stimulator device 22, each electrically-conductive body 28 or 30 is formed of a somewhat rectangular piece of metal (e.g. steel) which has been shaped to form a shallow C (corresponding substantially to the contour of the band 26) and is rigidly secured to the band 26 with a bolt 44 so that the bodies 28 and 30 are electrically connected to the band 26. The bodies 28 and 30 are not intended to conduct electrical current to the material of the band 26 during use of the stimulator device 22 but must be electrically connected to one another for purposes of generating the desired electromagnetic field within the band 26.

By way of example, each body 28 or 30 has a length of about 2.25 inches, a width of about 1.6 inches, and a thickness of about 0.5 inches.

Each coil 32 or 34 includes conducting material which is wound around the perimeter of a corresponding body 28 or 30 in a layered manner and which forms both coils 32 and 34. In other words, the conducting material forming one coil 32 is wrapped about its corresponding body 28 and then extends to the other body 30 where it is wrapped about the body 30 to form the coil 34. Thus, the same conducting material forms both coils 32 and 34, and the coils 32 and 34 are thereby connected in series with one another. The coils 32 and 34 also include an insulating cover 46 which is wrapped about the conducting material to electrically insulate the coils 32, 34 from the corresponding bodies 28, 30. Two end portions, indicated 48 and 50 in FIG. 3, of the conducting material are accessible from beneath the insulating cover 46 to accommodate the connection of conducting wire (described herein) thereto.

With reference again to FIGS. 1 and 2, the current-altering means 24 can take any number of forms for altering the flow of DC current through the system 20. However, in the depicted system 20, the current-altering means 24 includes resistance means wired in-line with the coils 32, 34 wherein the resistance means includes a pair of light bulbs 52, 54 (and corresponding light bulb receptacles 53, 55 for supporting the bulbs 52, 54) which are wired in parallel with one another yet in-line with the coils 28 and 30, as best shown in the wiring diagram of FIG. 2. In addition, an ON/OFF switch 56 is wired in-line with one of the bulbs 54 for selectively permitting or preventing current flow through the bulb 54. As will be apparent herein, with the switch 56 switched OFF, current is permitted to flow through only one bulb 54 and through the coils 28, 30, and with the switch 56 switched ON, current is permitted to flow through both bulbs 52, 54. It follows that since more current is necessary to operate the two bulbs 52, 54 than one bulb alone, more current flows through the coils 28, 30 when the switch 56 is switched ON than is the case when the switch 56 is switched OFF. Thus, the bulbs 52, 54 and switch 56 provide an effective means of altering the current flow through the coils 28, 30 (between two current flows) and therefore provides a means for selectively treating body tissue with the stimulator 22 at a low current setting and a higher current setting.

In the depicted system 20, the bulbs 52, 54 are each rated at fifty Watts, but alternative bulb sizes can be used. In addition, the bulbs 52, 54 and switch 56 are mounted within a vertically-oriented control panel 60 to enhance the ease with which the system 20 can be switched between the low and higher current settings and to enable the user to determine at a glance (i.e. by the glow of one bulb or two bulbs) whether the system 20 is set on either the low current setting or the higher current setting.

As far as the wiring of the system 20 is concerned and as best shown in FIG. 2, one wire 80 is connected between the coil 34 and the bulb 52, and the ON/OFF switch 56 is connected in-line between the bulbs 52 and 54. In addition, a wire 82 is connected to the bulb 54 and provides a first lead 90 to which DC current is permitted to flow from the DC current source 23, and a wire 84 extends from the bulb 52 and is joined to the wire 82 at a junction 86. Still further, a wire 88 is connected to the coil 32 and provides a second lead 92 to which DC current is permitted to flow from the DC current source 23. Therefore, DC current is permitted to complete its flow through the system 20 by way of the first and second leads 90 and 92.

With reference again to FIGS. 1 and 2, the means 23 through which DC current is delivered to the stimulator 22 is in the form of a battery charger 62 which plugs into a wall (e.g. 110 volt) outlet 64 and converts AC current from the outlet 64 to DC current for use within the system 20. In this connection, the charger 62 includes an input plug 66 which plugs into the outlet 64 and through which input current is permitted to flow and negative and positive outlet leads 68 and 70, respectively, through which output current is permitted to flow. At the ends of the outlet leads 68 and 70 are alligator clips 72 and 74 with which the leads 68 and 70 can be readily attached to the first and second leads 90 and 92 leading from the junction 86 and coil 32, respectively.

The battery charger 62 can be of any of a number of brands having any of a number of input/output capabilities but in the depicted system 20 is wired to accept 120 (AC) volts at its input and produce 12.6 (DC) volts at its output. An example of such a battery charger is a Schauer battery charger bearing the designation Japlar/Schauer and which is available from Japlar Acquisition Co. of Cincinnati, Ohio. As will be apparent herein, upon connecting the alligator clips 72, 74 to the first and second leads 90 and 92, respectively (so that the current flows through the coils 32 and 34 before it flows through the bulbs 52, 54) the electromagnetic field generated, or induced, within the interior opening of the band 26 is believed to be more positive (than negative), and upon connecting the alligator clips 72, 74 to the second and first leads 92 and 90, respectively (so that the current flows through the coils 32 and 34 after it flows through the bulbs 52, 54), the electromagnetic field generated within the interior opening of the band 26 is believed to be more negative (than positive). The capacity to selectively connect the alligator clips 72, 74 to the leads 90, 92 so that the field generated within the band 26 is either more-positive or more-negative is advantageous in that it permits the field generated within the band 26 to be readily switched between the more-positive field or the more-negative field depending upon whether the tissue desired to be treated will be better served with a more-positive field or a more-negative field.

Figure 4:
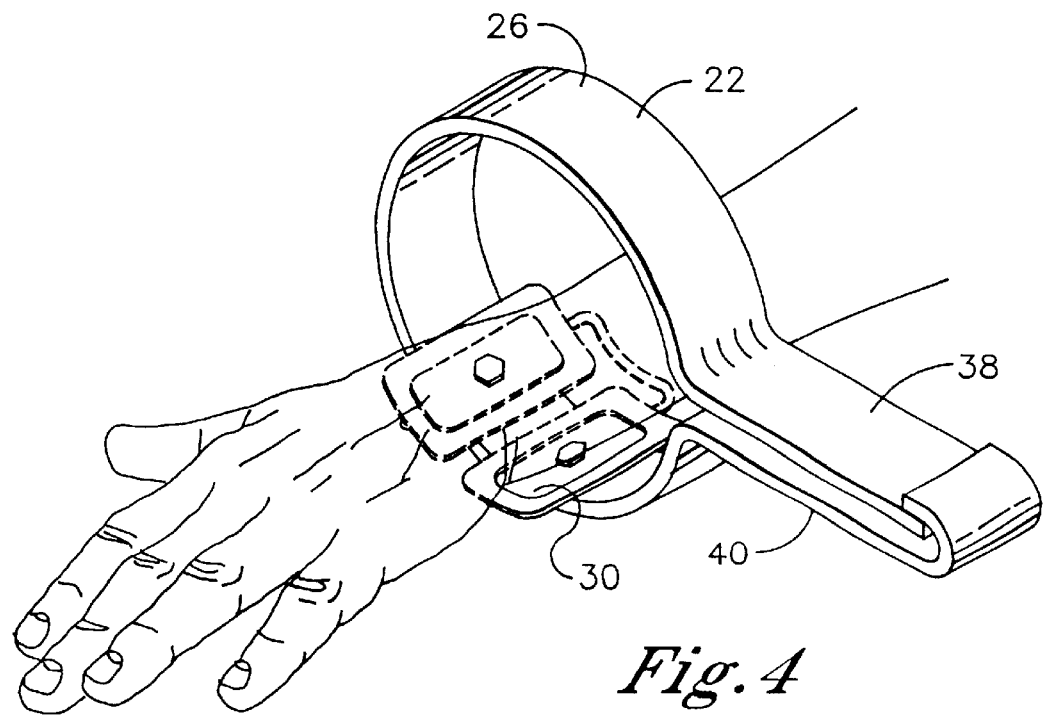
FIG. 4 is a perspective view of a hand being positioned within the stimulator device of FIG. 3 for use of the system.

To use the system 20 in a treatment process, the region or area of tissue to be treated is positioned within the band 26, and the band (which can be switched in either a one-bulb mode or a two-bulb mode to dictate the current flow through the coils 32, 34) is left undisturbed about the tissue to be treated for a predetermined period of time (e.g. about thirty minutes at a time). For example and with reference to FIG. 4, to treat an area of the wrist of an individual, the individual's wrist is positioned within the band 26 so that the area to be treated is positioned substantially centrally of the band 26. Whether the system is switched to induce a more-positive electromagnetic field within the band 26 or a more-negative electromagnetic field within the band 26 may be dictated by the make-up or composition of the tissue to be treated. For example, bones include a large amount of calcium—which possesses a positive valance. Therefore, by exposing bones to be treated to a more-negative electromagnetic field, calcium is more likely to be attracted to the area and thus promote bone healing.

In one case study, an individual's hand had been broken between the thumb area and the wrist, and several months (i.e. approximately one year) of conventional treatment (including confining the set bones within a cast and subsequently removing the cast) did not remove the pain from the region of the break nor did the bone heal. Following four weeks of treatment with the system 20 and the device 22 described herein (wherein the bones to be treated were positioned within the band 26 of the device 22 twice a day for about thirty minutes per session and the system 20 was wired to induce a more negative field within the band 26), the treated region was rendered pain-free, and the bone was completely healed.

In another case study, an individual's wrist had been broken in several places, and conventional treatment did not adequately repair the bones or remove the pain that the individual was experiencing. In fact, the undue length of time that the bones were taking to heal led the doctors who were treating the individual to recommend surgery. However, following four weeks of treatment with the device described herein (wherein the wrist bones to be treated were positioned within the band 26 of the device 22 twice a day for about thirty minutes per session and the system 20 was wired to induce a more negative field within the band 26) adequately repaired the damage (i.e. the bones completely healed), rendered the wrist pain-free, and surgery was avoided.

In still another case study, an individual had broken his leg in thirteen places in a skiing accident. The region of the breaks were located at and just above the individual's ankle, and conventional treatment required the use of pins and screws to adequately hold the bones in place while they healed. Following such conventional treatment and the use of the stimulator device 22 for a short period of time, the individual continued to experience a constant pain and numbness in the affected region of the leg. By using the device 22 described herein for about forty days (wherein the leg bones to be treated were positioned within the band 26 of the device 22 twice a day for about thirty minutes per session and the system 20 was wired to induce a more-negative field within the band 26) the bones were believed to be adequately healed and most of the pain was relieved, but some numbness persisted. At that point, the system 20 was switched to induce a more-positive field within the band 26 and the treatments were re-started. After several days, the remaining numbness disappeared.

In still another case study, an individual had lost feeling in one of his hands following open heart surgery. (It was believed that his arms had been pulled back too far in preparation of or during the surgery procedure, thereby inducing nerve damage in the individual's elbows.) Following about one month of treatment with the aforedescribed device 22 (wherein the treatment included thirty minute sessions, twice a day), nerve damage to the elbows was repaired and feeling in several fingers (i.e. most) of the affected hand was restored.

In yet another case study, an individual had broken bones in his pelvic region in several places in a motorcycle wreck. Following a six-month period during which the pelvic bone healed, an area of the tailbone covering about four inches in length had not healed. (X-rays revealed that a four inch crack in the tailbone remained separated.) The tailbone area was subsequently treated with magnetic stimulation over a six month period (with both positive and negative-charged electrodes) but still, the tailbone did not heal and the pain did not go away. The area was then treated with a system and device similar to the system 20 and device 22 described herein, except that the band of the system was made large enough to encircle the individual's body so that the band could span the affected area during treatment. The treatments (thirty minute sessions, twice a day—and wherein the current flow through the coils were about four amps due to the switching of the device to a one bulb mode) continued for about one month, after which time most of the pain had disappeared and most of the four-inch crack healed. (X-rays at this point showed that only about a one-inch crack in the tailbone had not healed.) Then a flexible steel plate which was large enough to cover the entire tailbone area was attached to the band, and the current flow through the coils was subsequently changed to a more-positive current and doubled to eight amps (by switching the device to the two-bulb mode). Treatments with the modified band and the increased current flow continued for a period of two weeks, after which time the pain of the affected area totally disappeared. The individual in this case study has not had another X-ray to date.

Figure 5:
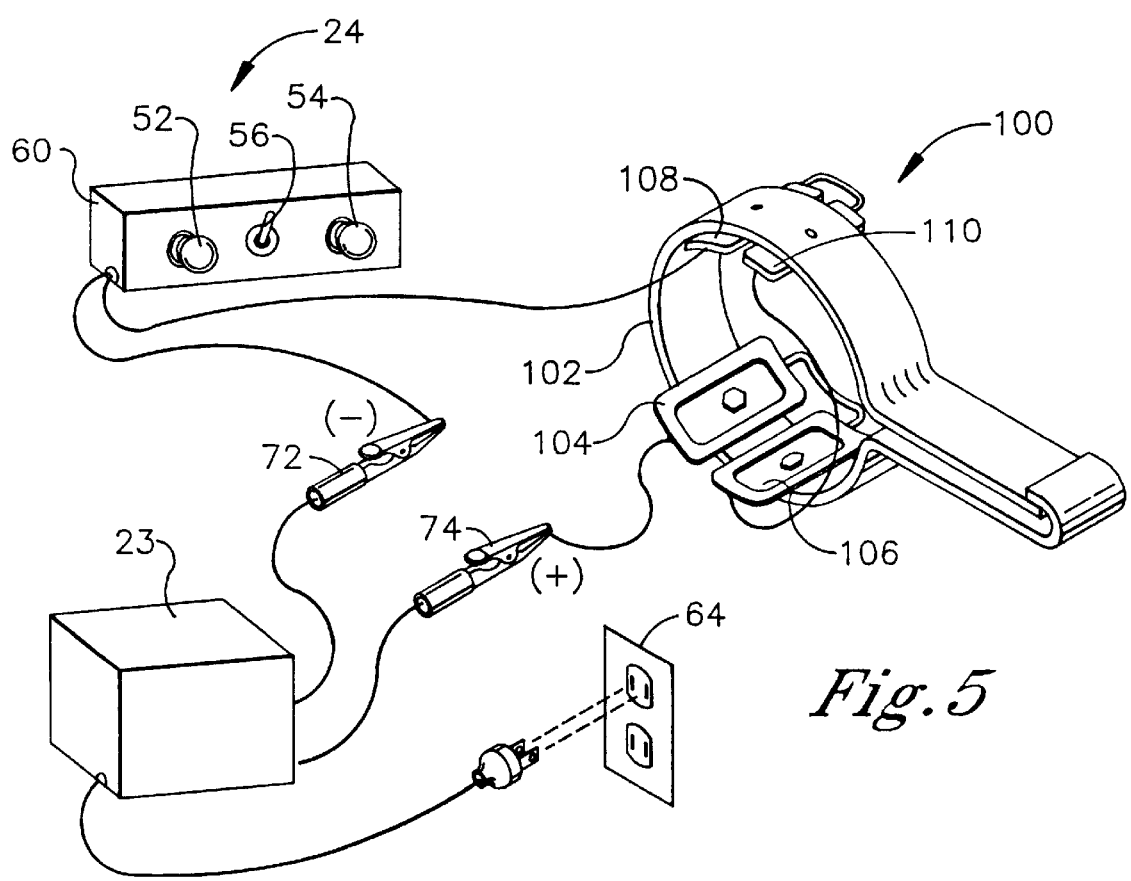
FIG. 5 is a perspective view of an alternative embodiment of a stimulator system within which features of the invention are incorporated.

It will be understood that numerous modifications and substitutions can be had to the aforedescribed embodiment without departing from the spirit of the invention. For example, although the aforedescribed embodiment 20 has been shown and described as including two coils 32, 34 mounted within its band 26, an embodiment in accordance with the broader aspects of this invention can include a band 26 having an alternative number of coils. For example, there is illustrated in FIG. 5 a system, indicated 100, having a band 102 within which four coils 104, 106, 108 and 110 (and corresponding electrically-conductive bodies, e.g. pole shoes) are mounted. (Other components of the system 20 which are identical to those of the system 20 of FIGS. 1–4 bear the same reference numerals.) In the depicted FIG. 5 system 100, the coils 104, 106, 108 and 110 are connected in series with one another so that DC current flows in sequence through the coils 104, 106, 108 and 110, and the system 100 may be preferred over the aforedescribed system 20 if a stronger electromagnetic field is desired to be induced within the band 102. It will be understood that although the coils 104, 106, 108 and 110 are wired in series with one another, an alternative system can be wired in an alternative manner to induce, for example, a more-positive field within one coil (or set of coils) and a more-negative field within another coil (or set of coils) by wiring a coil (or set of coils) to receive current flow in advance of a bulb and wiring another coil (or set of coil) to receive current flow after it flows through a bulb.

Further still, although the aforedescribed system 20 of FIGS. 1–4 has been shown and described as including a single device 22 operated by a single battery charger 62, it will be understood that a system in accordance with the present invention can include multiple devices operable by a single battery charger. Accordingly, the aforedescribed embodiments are intended for the purpose of illustration and not as limitation.

What is claimed is:

1. An electromagnetic stimulator system for treating body tissue, the system comprising:

an electrically-conductive band having an interior opening sized to accept body tissue desired to be treated with the stimulator system;

a body of electrically-conductive material secured to the band in electrically-conducting relationship therewith;

an insulated coil encircling the body of the electrically-conductive material so that when a DC current is conducted through the coil, an electromagnetic field is induced through the body of electrically-conductive material which, in turn, induces an electromagnetic field within the interior opening of the band; and means for delivering DC current through the coil so that by positioning the body tissue to be treated within the electrically-conductive band and delivering DC current through the coil, the body tissue positioned within the band is exposed to the electromagnetic field induced within the interior opening of the band.

2. The system as defined in claim 1 further including means connected to the coil for selectively altering the flow of DC current which is delivered to the coil between one and another current flow so that the body tissue positioned within the band can be treated by the electromagnetic field induced by the one or another flow of DC current through the coil.

3. The system as defined in claim 2 wherein the means for altering the flow of DC current through the coil includes resistance means wired in-line with the coil.

4. The system as defined in claim 3 wherein the resistance means includes at least one light bulb wired in-line with the coil assembly.

5. The system as defined in claim 3 wherein the resistance means includes two light bulbs wired in parallel to one another and in-line with the coil, and the means for altering further includes a switch associated with one of the light bulbs for selectively permitting or shutting off the flow of current through said one bulb.

6. The system as defined in claim 1 wherein the body of electrically-conductive material attached to the band is the pole shoe of a starter of an internal combustion engine and the coil which encircles the body of electrically-conductive material is the coil which encircles the pole shoe in the starter of the internal combustion engine.

7. The system as defined in claim 1 wherein the system includes a plurality of bodies of electrically-conductive material secured to the band and in electrically-conducting relationship therewith, and includes a plurality of insulated coils connected in series relationship with one another and wherein each coil encircles a corresponding body of electrically-conductive material so that when a DC current is conducted through the plurality of insulated coils, an electromagnetic field is induced through the bodies of electrically-conductive material which, in turn, induces an electromagnetic field within the interior opening of the band.

8. The system as defined in claim 1 wherein the band has a width which is at least as broad as the body tissue to be treated with the stimulator system so that when the body tissue to be treated is positioned within the band, the band spans the body tissue to be treated.

9. The system as defined in claim 1 wherein the means for delivering DC current to the coil is adapted to accept AC current from a source of AC power and convert the AC current to DC current for delivery to the coil.

10. The system as defined in claim 9 wherein the means for delivering DC current to the coil is a battery charger.

11. A method for treating body tissue with an electromagnetic field including the steps of:

providing an electromagnetic stimulator system including
a) an electrically-conductive band having a central opening sized to accept body tissue desired to be treated with the stimulator system;
b) a body of electrically-conductive material secured to the band in electrically-conducting relationship therewith;
c) an insulated coil encircling the body of the electrically-conductive material so that when a DC current is conducted through the coil, an electromagnetic field is induced through the body of electrically-conductive material which, in turn, induces an electromagnetic field within the interior opening of the band; and
d) means for delivering DC current through the coil;

positioning the body tissue to be treated within the electrically-conductive band, and delivering DC current through the coil so that the body tissue positioned within the band is exposed to the electromagnetic field induced within the interior opening of the band.

12. The method as defined in claim 11 wherein the time with which the body tissue is treated with the system is monitored so that the body tissue is not exposed to the electromagnetic field generated within the band for more than about thirty minutes at a time.

13. The method as defined in claim 11 wherein the provided stimulator system includes means connected to the coil for selectively altering the flow of DC current which is delivered to the coil between one current flow and another current flow so that the body tissue positioned within the band can be treated by the electromagnetic field induced by the one or another flow of DC current through the coil.

14. The method as defined in claim 13 wherein the means for selectively altering includes resistance means wired in-line with the insulated coil between the means for delivering DC current to the coil and the coil so that current flow from the DC current source flows through the resistance means before flowing through the coil.

15. The method as defined in claim 13 wherein the means for selectively altering includes resistance means wired in-line with the insulated coil between the means for delivering DC current to the coil and the coil so that current flow from the DC current source flows through the coil before flowing through the resistance means.

* * * * *